US006451524B1

(12) United States Patent
Ecker

(10) Patent No.: US 6,451,524 B1
(45) Date of Patent: Sep. 17, 2002

(54) IDENTIFICATION OF DISEASE PREDICTIVE NUCLEIC ACIDS

(75) Inventor: David J. Ecker, Encinitas, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 7 days.

(21) Appl. No.: 09/200,355

(22) Filed: Nov. 25, 1998

(51) Int. Cl.$^7$ .......................... C12Q 1/68; C07H 21/04
(52) U.S. Cl. ........................ 435/6; 536/23.1; 536/24.31
(58) Field of Search .................... 435/6, 375; 536/23.1, 536/24.31

(56) References Cited

U.S. PATENT DOCUMENTS

| | | | | | |
|---|---|---|---|---|---|
| 5,582,972 | A | * | 12/1996 | Lima et al. | 435/6 |
| 5,866,698 | A | * | 2/1999 | Ecker et al. | 536/24.5 |
| 5,885,834 | A | * | 3/1999 | Epstein | 435/375 |
| 5,962,673 | A | * | 10/1999 | Monia et al. | 536/24.5 |
| 5,977,311 | A | * | 11/1999 | Nandabalan et al. | 530/358 |
| 6,221,587 | B1 | * | 4/2001 | Ecker et al. | |

OTHER PUBLICATIONS

Klaff et al. "RNA structure and the regulation of gene expression" Plant Molecular Biology, vol. 32, pp. 89–106, Oct. 1996.*
Dandekar et al. "Finding the hairpin in the haystack: serching for RNA motifs" Trends in Genetic, vol. 11, No. 2, pp. 45–50, Feb. 1995.*
Balvay et al. "Pre–mRNA Secondary Structure and the regulation of Splicing" BioEssays, vol. 15, No. 3, pp. 165–169, Mar. 1993.*
Harries et al. "Strategies for targeted gene therapy" Trends in Genetics, vol. 12, No. 10, pp. 400–405, Oct. 1996.*
Trends Genetics, "The G–tetrad in antisense targeting" Trends in Genetics, vol. 12, No. 8., pp. 90–91, Aug. 1996.*
Marshall et al "Gene therapy's growing pains" Science, vol. 269, pp. 1050–1055, Aug. 1995.*
Franch et al. "Programmed Cell Death by hok/sok of Plasmid R1: Processing at the hok mRNA 3' end triggers structurall rearrangemetns that allow translation and antisense RNA binding" JMB, vol. 273, No. 1, pp. 38–51, Oct. 17, 1997.*
Franch et al. "Programmed Cell Death by hok/sok of Plasmid R1 copuled nucleotide covariations reveal a phylogenetically conserved folding pathway in the hok family of mRNAs" JMB, vol. 273, No. 1, pp. 26–37, Oct. 17, 1997.*
Benson et al., "GenBank", Nucl. Acids Res., 1998, 26(1), 1–7.
Brown, J.W., "Phylogenetic analysis of RNA structure on the Macintosh computer", CABIOS Commun., 1991, 7(3), 391–393.
Edwalds–Gilbert, "Alternative poly(A) site selection in complex transcription units: means to an end?", Nucl. Acids Res., 1997, 25(13), 2547–2561.

Gautheret et al., "Identification of Base–triples in RNA using Comparative Sequence Analysis," J. Mol. Biol., 1995, 248, 27–43.
Gautheret et al., "G U base pairing motifs in ribosomal RNA", RNA, 1995, 1, 807–814.
Gautheret et al., "Inferring the conformation of RNA base pairs and triples from patterns of sequence variation", Nucl. Acids Res., 1997, 25(8), 1559–1564.
Gautheret, "Alternate to Polyadenylation in Human mRNAs: A Large–Scale Analysis by EST Clustering", Genome Res., 1998, 8, 524–530.
Gutell, "Collection of small subunit (16S–and 16S–like) ribosomal RNA structures: 1994", Nucl. Acids Res., 1994, 22(17), 3502–3507.
Gutell, "Collection of small subunit (16S–and 16S–like) ribosomal RNA structures", Nucl. Acids Res., 1993, 21(13), 3051–3054.
Gutell, "A compilation of large subunit (23S and 23S–like) ribosomal RNA structures: 1993", Nucl. Acids Res., 1993, 21(13), 3055–3074.
Gutell et al., "Comparative Sequence Analysis of Experiments Performed During Evolution", in Ribosomal RNA Group I Introns, Green (ed.), Austin: Landes, 1996, Ch. 2, 15–33.
Kuhl et al., "Spontaneous overexpression of the long form of the Bcl–X protein in a highly resistant P388 leukaemia", Br. J. Cancer, 1997, 75(2), 268–274.
Laferriere et al., "An RNA pattern matching program with enhanced performance and portability", Comput. Appl. Biosci., 1994, 10(2), 211–212.
Landers et al., "Transitional Enhancement of mdm2 Oncogene Expression in Human Tumor Cells Containing a Stabilized Wild–Type p53 Protein", Cancer Res., 1997, 57, 3562–3568.
Lodmell et al., "Genetic and comparative analyses reveal an alternative secondary structure in the region of nt 912 Escherichia coli 16S rRNA", Proc. Natl. Acad. Sci. USA, 1995, 92, 10555–10559.

(List continued on next page.)

Primary Examiner—Jeffrey Fredman
Assistant Examiner—Jeanine Goldberg
(74) Attorney, Agent, or Firm—Woodcock Washburn LLP

(57) ABSTRACT

The present invention is directed to methods of identifying target nucleic acid sequences which are predictive of preselected disease states or biological conditions in cells containing the nucleic acid sequence. Members of a set of mRNA molecules from a common gene, but containing different sequences and structures, are compared. The gene is predictive of the disease state or biological condition in cells containing the gene. At least one molecular interaction site from among those present in the members of the set are identified. The molecular interaction site is present in cells likely to have the disease state or biological condition. At least one nucleic acid sequence from the molecular interaction site is ascertained.

9 Claims, 3 Drawing Sheets

OTHER PUBLICATIONS

Müller–Pillasch et al., "Cloning of Novel Transcripts of the Human Guanine–Nucleotide–Exchange Factor Mss4: In Siu Chromosomal Mapping and Expression in Pancreatic Cancer", *Genomics,* 1987, 46, 389–396.

Scott et al., "A Truncated Intracellular HER2/neu Receptor Produced by Alternative RNA Processing Affects Growth of Human Carcinoma Cells", *Mol. Cell Biol.,* 1993, 13(4), 2247–2257.

Sutton et al., "TIGR Assembler: A New Tood for Assembling Large Shotgun Sequencing Projects", *Genome Science & Tech.,* 1995, 1(1), 9–19.

Thompson et al., "CLUSTAL W: improving the sensitivity of progressive multiple sequence alignment through sequence weighting, position–specific gap penalties and weight matrix choice", *Nucl. Acids Res.,* 1994, 22(22), 4673–4680.

Woese et al., "Evidence for several higher order structural elements in ribosomal RNA", *Proc. Natl. Acad. Sci. USA,* 1989, 86, 3119–3122.

Woese et al., "Secondary structure model for bacterial 16S ribosomal RNA: phylogenetic, enzymatic and chemical evidence", *Nucl. Acids Res.,* 1980, 8(10), 2275–2293.

Zhang et al., "Gene Expression Profiles in Normal and Cancer Cells", *Science,* 1997, 276, 1268–1272.

U.S. application No. 09/076,440, Ecker et al., filed May 12, 1998.

* cited by examiner

IDENTIFICATION OF DISEASE PREDICTIVE NUCLEIC ACIDS

FIELD OF THE INVENTION

The present invention is directed to methods of identifying target nucleic acid sequences which are predictive of disease states or biological conditions in cells containing the nucleic acid sequence.

BACKGROUND OF THE INVENTION

Recent advances in genomics, molecular biology, and structural biology have highlighted how RNA molecules participate in or control many of the events required to express proteins in cells. Rather than function as simple intermediaries, RNA molecules actively regulate their own transcription from DNA, splice and edit mRNA molecules and tRNA molecules, synthesize peptide bonds in the ribosome, catalyze the migration of nascent proteins to the cell membrane, and provide fine control over the rate of translation of messages. RNA molecules can adopt a variety of unique structural motifs, which provide the framework required to perform these functions.

The many functions of RNA molecules has also solidified their importance as therapeutic drug and diagnostic targets. Indeed, many investigators are pursuing mRNA transcripts and proteins produced therefrom that are expressed at different levels in cancer vs. normal cells in order to develop therapeutic and/or diagnostic compounds which modulate the cancer-causing mRNA transcript or protein. Indeed, 500 transcripts have been reported to be expressed at significantly different levels (15-fold on average) in normal vs. gastrointestinal tumor cells. Zhang, et al., *Science*, 1997, 276, 1268–72. Many genes have as many as 10–20 alternative transcript forms that, in some cases, have been associated with a cancer phenotype. For example in cancerous cells, transcription of the mdm2 gene is initiated at a distinct site not used in normal cells. Landers, et al., *Cancer Res.*, 1997, 57, 3562–3568, incorporated herein by reference in its entirety. In the Bcl-x mRNA, alternatively spliced forms of the transcript result in dramatically different cell behavior and sensitivity to chemotherapeutic drugs. Kuhl, et al., *Br. J. Cancer*, 1997, 75, 268–274, which is incorporated herein by reference in its entirety.

A universal technology platform to attack multiple forms of cancer has widely been believed to be impossible due to the heterogeneous nature of cancer. Thus, traditional cancer therapeutics has focused on individual cancer pathways and modulation of individual proteins and/or mRNA transcripts associated with the suspected causative pathway of the disease state. An unconventional, broadly applicable approach to cancer diagnosis and treatment, however is greatly desired. Accordingly, the present invention provides the means to identify distinguishing features of types of cancer coupled with a common molecular mechanism to diagnose and selectively destroy the cancer cells or other cells associated with a disease state or biological condition. It is a principal object of the invention to identify a target nucleic acid sequence which is predictive of a disease state or biological condition in cells containing the nucleic acid sequence.

SUMMARY OF THE INVENTION

The present invention is directed to methods of identifying target nucleic acid sequences which are predictive of preselected disease states or biological conditions in cells containing the nucleic acid sequence. Members of a set of mRNA molecules from a common gene, but containing different sequences and structures, are compared. The gene is predictive of the disease state or biological condition in cells containing the gene. At least one molecular interaction site from among those present in the members of the set are identified. The molecular interaction site is present in cells likely to have the disease state or biological condition. At least one nucleic acid sequence from the molecular interaction site is ascertained.

The present invention is directed to methods of identifying target nucleic acid sequences which are predictive of preselected disease states or biological conditions, especially cancer, in cells containing the nucleic acid sequence. Members of a set of mRNA molecules from a common gene, but containing different sequences and structures, are compared. The set of mRNA molecules from a common gene, but containing different sequences and structures are referred to as "alternative transcript forms." Comparison of the alternative transcript forms provides for the identification of at least one alternative transcript form which is associated with the disease state or biological condition. The alternative transcript form, or the protein which is encoded by the same, is not required to be directly involved in any pathogenesis pathway. For example, the alternative transcript form may be merely a marker for the disease state or biological condition without participating or being required for establishment or maintenance of the disease state or biological condition. For example, the alternative transcript form or protein encoded thereby may be a by-product of the pathogenesis involved in the disease state or biological condition. Once an alternative transcript form, which is associated with a disease state or biological condition is identified, the molecular interaction site, or cancer signature, for example, can be identified by the methods described herein. The molecular interaction site is unique to the alternative transcription form which is associated with the disease state or biological condition. The alternative transcription forms which are not associated with a disease state or biological condition do not contain the identified molecular interaction site. Once the molecular interaction site is identified, additional alternative transcript forms from a variety of genes can be analyzed to determine whether they comprise the same molecular interaction site. In this manner, additional mRNA molecules can be identified which may also be predictive of a disease state.

Figure 1:
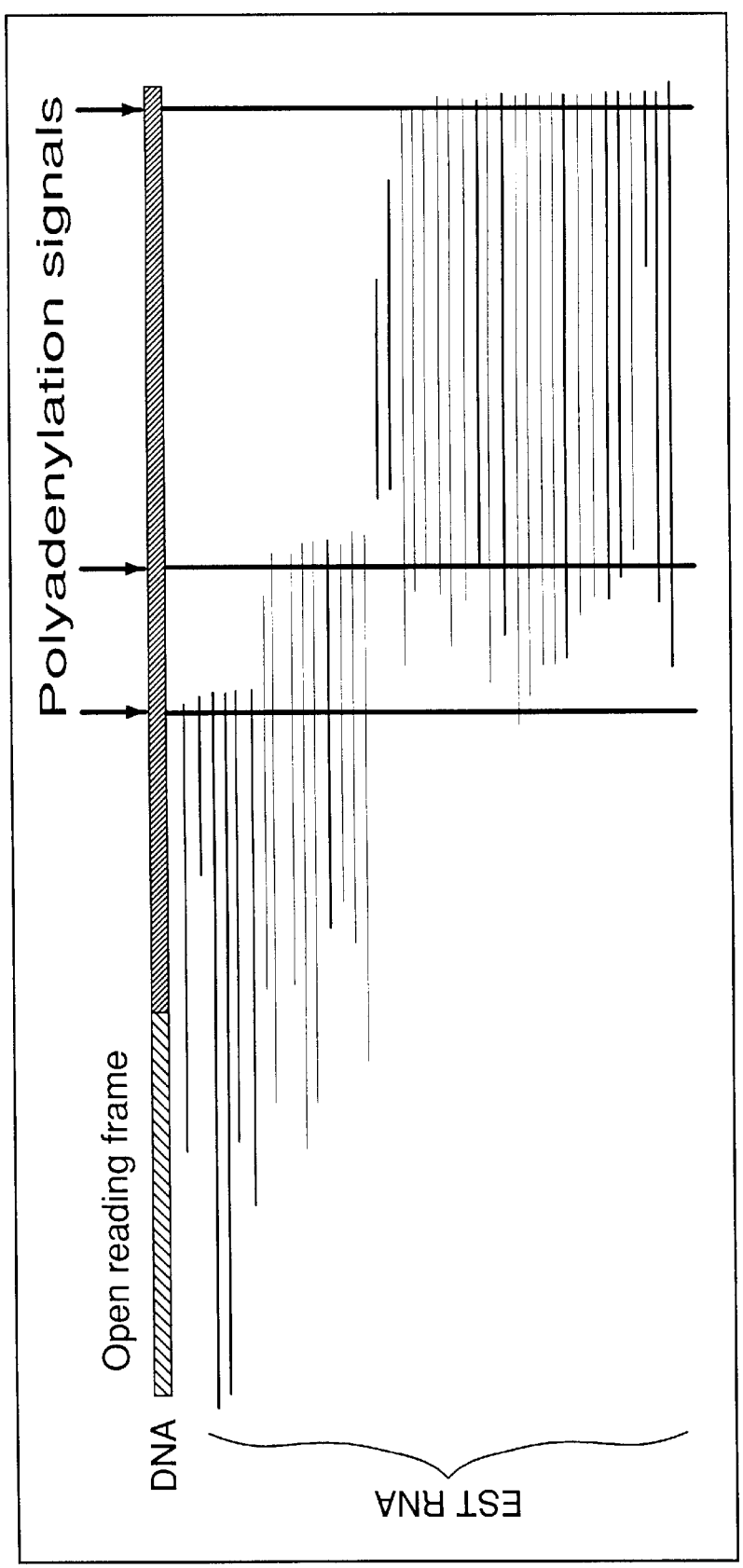
FIG. 1 illustrates an example of a 3'-EST cluster.

Alternative transcript forms originate from alternative initiation of transcription, alternative splicing, alternative 3'-end processing or a combination of these mechanisms. Alternative 3'-end processing may be the greatest source of alternative transcript forms. Studying 160,000 EST sequences, D. Gautheret and collaborators have shown that from 20–40% of the transcripts have two or more different 3'-ends (See FIG. 1) Gautheret, *Genome Res.*, 1998, 8, 524–530, which is incorporated herein by reference in its entirety. Other investigators have shown that certain classes of mRNAs are alternatively 3'-end processed in a tissue-specific or developmentally-specific pattern (Edwalds- Gilbert, *Nucl. Acids. Res.*, 1997, 25, 2547–2561, which is incorporated herein by reference in its entirety) and in some cases this has been correlated with cancer. For example, the mss4 transcript was recently shown to have alternative 3'-end processing in pancreatic cancer. Muller-Pillasch, *Genomics*, 1887, 46, 389–396, which is incorporated herein by reference in its entirety. Alternative 3'-end formation does not change the protein composition, but can dramatically influence message stability and regulate translation by including or excluding regulatory sequences in the mRNA transcript.

Figure 2:
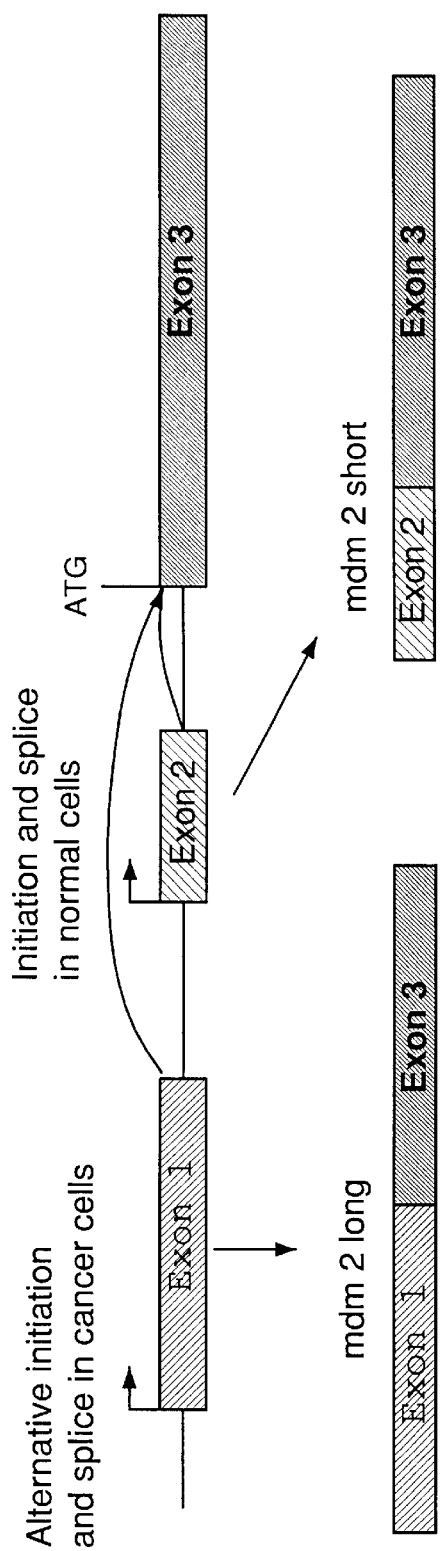
FIG. 2 illustrates alternative initiation of mdm2 gene in cancer and normal cells results in unique RNA structures (SEQ ID NO: 1, left, and SEQ ID NO: 2, right).
Figure 2:
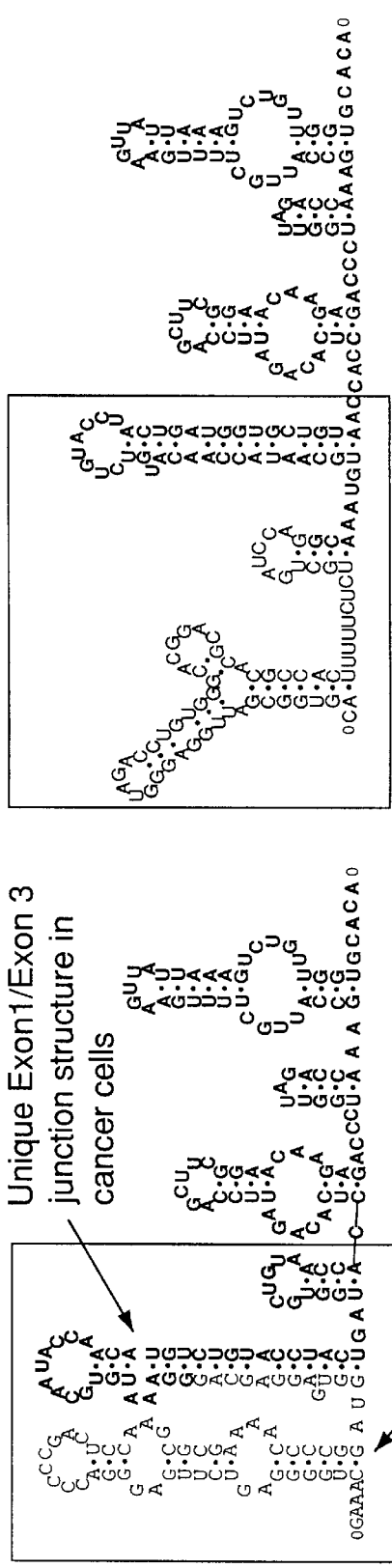

Alternative transcript forms, despite being transcribed from identical DNA and translated into identical proteins possess unique sequences and three-dimensional shapes that exist only at the level of RNA. A very important consequence of alternative transcript forms for cancer recognition is the unique shapes that they adopt. In contrast to the regular, helical nature of DNA, RNA strands form intricate stems, loops, and bulges, which are arranged into three-dimensional shapes that rival proteins in their complexity. Alternative transcript forms can produce different shapes in several ways. First, with alternative transcription initiation or 3'-end formation, there are unique sequences in mRNAs that do not appear at all in the normal mRNA (See, FIG. 2). These sequences, in turn, will fold into unique structures within themselves and with the adjacent RNA. Second, each alternative splicing event can produce a unique junction, in which the adjacent RNA on each side of the junction will re-arrange into a new three-dimensional shape.

Alternative transcript forms are distinguishable from cancer-specific expression of transcripts. Cancer-specific transcripts provide a perfectly useful set of molecular targets for the invention described herein. However, the greater opportunity to find useful cancer signatures is in alternative transcript forms since there may be 2–20 different forms of every transcript and 10–20,000 genes expressed in any given cell. Thus, the opportunity to find cancer-specific alternative transcript forms may be much greater than for cancer-specific transcripts. Whether the origin of the cancer signature comes from cancer-specific transcripts or cancer-specific transcript forms, for the technology of the present invention it is not required that the cancer-specific differences in mRNA be responsible for cancer phenotype. It is not even important that it is known what they do. The important point is that they are present in cancer cells and can therefore be used to mark them for destruction. Accordingly, the presented invention is directed, in part, to identifying at least one molecular interaction site within at least one alternative transcript form which is associated with the disease state or biological condition.

Alternative transcript forms and their association to particular disease states or conditions are known to one skilled in the art. For example, alternative transcript forms known to those skilled in the art are shown in Table 1 below and are described in more detail in Edwalds-Gilbert, *Nucl. Acids. Res.*, 1997, 25, 2547–2561, which is incorporated herein by reference in its entirety. Any of the alternative transcript forms listed in Table 1, Table 2, and Table 3 can be used to identify molecular interaction sites as set forth below. Table 1 shows numerous examples of transcription units with multiple poly(A) sites, all within a single 3'-terminal exon. Included in Table 1 are those genes for which there is solid evidence for more than one RNA species. Two other major classes of gene organization leading to the generation of alternative poly(A) sites on mRNA are listed in Tables 2 and 3. The final protein products of both types of genes can differ at their C-termini depending on which processing pathway is followed. Exons are generally categorized as 5'-terminal, internal or 3'-terminal with polyadenylation signals in the UTR.

A number of genes listed in Table 2 contain composite exons in which 5' splice sites can sometimes be silent, causing them to behave as 3'-terminal exons, or sometimes be active, thereby causing them to behave as internal exons, depending on the tissues in which the gene is expressed; these we call composite, in/terminal exons. Genes like the immunoglobulin heavy chains have an exon serving either as the first 3'-terminal exon in one mRNA (use of pA1) or as an internal exon in a second mRNA which ends with a normal 3'-terminal exon found further downstream (use of pA2). The primary transcript from other genes like calcitonin/calcitonin gene-related peptide, listed in Table 3, are processed into two mRNAs by using either the first alternative 3'-terminal exon with its poly(A) site (pA1) or skipping that exon entirely and splicing the second 3'-terminal exon into the transcript, using pA2 instead. The distance between the poly(A) sites in these two classes of genes can be quite large (>3 kb in Ig genes) and differential sites of transcription termination, between the poly(A) sites, could change the distribution of 3'-end use in mRNA. Levels of basal polyadenylation factors, splicing factors and termination factors could all contribute cell type-specific mechanisms leading to 3'-end formation.

TABLE 1

Genes with alternative tandem poly(A) sites in the 3'-UTR

| Gene | Regulatory element[a] | Notable features Where seen | Comments |
| --- | --- | --- | --- |
| 23 kDa Transplantation antigen | | Brain, retina | From the P198 gene, which is highly conserved [including the poly(A) sites] across mammalian species; two poly(A) sites |
| α-Galactosidase A | | | Mouse; three poly(A) sites, two mRNAs |
| Acetylcholinesterase | | Muscle, brain | Mouse, human; two poly(A) sites; second site predominates in muscle, first site predominates in brain |
| Activin βA subunit | | TPA treatment | Human; eight possible poly(A) sites; treatment of HT1080 fibrosarcoma cells with TPA causes a shift over time to use of proximal poly(A) site |
| ADP ribosylation factor (ARF) | 3 (ARF 4) | Testes | ARF 1 has two poly(A) sites conserved in human and rat ARF 4 makes a short, testes-specific mRNA generated by alternative polyadenylation |
| Aldolase B | | | Mouse; one non-canonical and three canonical poly(A) sites, use of all four sites detectable in liver and kidney |
| Amphiglycan (syndecan 4, ryudocan) | | Chondrocytes | At least two poly(A) signals; longer message is ubiquitous, |

TABLE 1-continued

Genes with alternative tandem poly(A) sites in the 3'-UTR

| Gene | Regulatory element[a] | Notable features Where seen | Comments |
|---|---|---|---|
| | | | shorter is tissue-specific; switch in poly(A) site use during chondrocyte differentiation |
| Amyloid protein | 2, 4 | | Sequence between two poly(A) sites increases translation of the longer mRNA |
| Androgen receptor | | | Human; two poly(A) sites, the first if AUUAAA and the second is CAUAAA |
| Angiotensin converting enzyme (ACE) | | Testes, pulmonary tissue | Rabbit; testes- versus pulmonary-specific forms |
| Ankyrin-1 | | Brain | Mouse; both poly(A) sites used in erythroid tissues, distal site used in cerebellum |
| Apolipoprotein B | | Intestine | Putative cryptic poly(A) site improved by editing |
| Arylsulfatase A | | | Mutation of first poly(A) signal seen in arylsulfatase A pseudodeficiency |
| Axonin-1 | | Retina, brain | Chicken; three poly(A) sites |
| β-Tubulin | | HSV infection | Changes in the ratio of the two forms occur during HSV infection |
| β2-Microglobulin | | | Murine; two poly(A) sites |
| β3-Adrenergic receptor | | | Human; rat; two poly(A) sites |
| Band 7.2b gene | | Many cell types | Human; integral membrane phosphoprotein; distal site predominates in all tissues, proximal site use is significant in lung, liver and kidney and minimal in spleen |
| Brain-derived neurotrophic factor (BDNF) | | Heart, lung, brain | Rat; isoform production controlled by alternative splicing; multiple promoters used; two poly(A) sites, ratio of proximal; distal site use varies among heart, lung, cerebral cortex |
| Cationic amino acid transporter gene (cat-1) | 1 | Cell density | Rat; relative concentration of two mRNAs is regulated by cell density |
| c-Mos | 3 | | Porcine; protooncogene whose expression is restricted to gonadal tissues in the pig; alternative polyadenylation may play a role in translation |
| CD40 | 3 | Differentiation | murine; differential poly(A) site use during B lymphocyte activation |
| CD59 (membrane inhibitor of reactive lysis) | 3 | Many cell types | Human, complement regulatory protein; four possible poly(A) sites; use of two poly(A) sites varies in different cell lines |
| Chymotrypsin-like protease | | | Human chromosome 16q22.1; alternative polyadenylation creates transcription unit which overlaps with oppositely oriented gene |
| Clathrin heavy chain gene | 3 | Developmental changes | Mosquito; poly(A) site use differs between somatic cells and germ cells |
| Collagenase 3 | | | Human; three mRNAs seen in mammary carcinoma cells |
| cAMP-responsive element modulator (CREM) | 1 | Testes | Follicle-stimulating hormone regulates CREM expression in testes by changing poly(A) site use, causing an increase in mRNA stability |
| Cyclin D1 | | Developmental changes | Human, mouse, zebrafish; two poly(A) sites; change in poly(A) site use during zebrafish embryonic development; one major and two minor forms found in HeLa and all hematopoetic cells tested |
| Cyclooxygenase-1 (COX-1) | | | Human; two poly(A) sites |
| Cyclooxygenase-2 (COX-2) | 1 | Dexamethasone treatment | Expression induced by cytokines; three poly(A) sites; dexamethasone treatment selectively destabilizes longer mRNA |
| Cytochrome P450 aromatase | | Many cell types | Human; two poly(A) sites, [second poly(A) signal AUUAAA]; mouse, porcine, equine; two poly(A) sites, 2.5 kb mRNA predominant in ovaries |
| Cytochrome P450-linked ferredoxin | | | Mouse; two poly(A) sites |
| Dihydrofolate reductase (DHFR) | | Cell cycle | Seven poly(A) sites; promoter-proximal site used during growth stimulation |
| Dipeptidyl peptidase IV (CD26) | | | Mouse; two poly(A) sites in exon 26, proximal poly(A) site predominates in all tissues examined |
| DNA polymerase β | 3 | Testes; brain | Rat; the 1.4 kb transcript predominates in testes and has a poly(A) signal AAUGAA; 4 kb transcript predominates in brain |
| eIF-2α (translation initiation factor 2α) | 1, 4 | Testes | Two poly(A) sites; different ratio in different tissues; the longer mRNA is more stable in activated T cells; the shorter mRNA has increased translatability; third poly(A) site used in testes |
| eIF-4E (translation initiation factor 4E) | | Many cell types | Mouse; multiple poly(A) signals; 1.8 kb transcript predominates in mouse kidney and liver and in a pre-B cell line, S194. A 1.5 kb transcript is abundant in mouse thymus and in S194 cells. Minor mRNAs of 2.2 and 2.5 kb correspond to use of alternate poly(A) signals as well |
| eIF-5 (translation initiation factor 5) | | Testes | Mammalian; proximal poly(A) site used predominantly in testes, distal site favored in other tissues examined |
| Excision repair gene ERCC6 | | Testes | Human; presumed helicase; two poly(A) signals, first is AUUAAA: shorter mRNA is primarily expressed in testes |
| Fanconi anemia group C (FACC) | 3 | | Human; three poly(A) sites, longest transcript is most abundant and its poly(A) signal is AAUAAA; first two |

TABLE 1-continued

Genes with alternative tandem poly(A) sites in the 3'-UTR

| Gene | Regulatory element[a] | Notable features Where seen | Comments |
|---|---|---|---|
| | | | poly(A) signals are non-canonical; longest transcript contains a series of direct 35 bp repeats preceded by a 12 bp palindrome |
| Ferritin heavy chain | | Many cell types | Human; two poly(A) signals; tissue-specific differences in ratio of use (brain, skeletal muscle versus placenta, liver, pancreas) |
| Fibroblast growth factor (int-2) | 2 | Retinoic acid treatment | Mouse; both mRNAs inducible in F9 cell line by treatment with retinoic acid |
| Basic fibroblast growth factor (bFGF) | 2 | Cell density | Use of two poly(A) sites varies with cell density |
| Fibroglycan (syndecan 2) | | | Human; at least two functional poly(A) signals |
| FMR1 | | | Fragile X gene; two poly(A) sites |
| G protein γ subunit (D-G γl) | 3 | Many cell types | Drosophila; use of three different poly(A) sites is developmentally regulated and cell type specific: 2.6 kb transcript found in head, 1.3 kb transcript found in body, 1.1 kb transcript more abundant in head than in body |
| Gastric capthesin E | | | Human aspartic protease; two poly(A) sites |
| GATA-2 | | | Transcription factor; two poly(A) sites |
| Grg | | | Murine; related to the groucho transcript of the Drosophila Enhancer of split complex |
| Growth hormone receptor, avian | | | Alternative poly(A) stie in exon 5 generates short form, in the absence of alternative splicing, unlike mammalian counterpart |
| Heparan sulfate proteoglycan | | Liver, kidney | Rat; major cell surface heparan sulfate proteoglycan; three poly(A) sites used in most tissues, most proximal sites used only in liver and kidney |
| Herpes simplex virus type 1 (HSV-1) UL24 | | | Increased polyadenylation at weak viral sites via effects on host cell CstF 64-kDa |
| High mobility group 1 protein (HMG1) | | | Murine; three poly(A) sites |
| Histone H1° | 1 | Butyrate treatment | Mouse; differentiation-specific histone H1; two mRNAs, first poly(A) signal is AUUAAA; minor 0.9 kb mRNA becomes more stable during butyrate-induced dedifferentiation, mRNAs equally stable after treatment with actinomycin D |
| Huntington disease gene | | Brain | Use of distal poly(A) site predominates in brain; most other tissues favor proximal poly(A) site |
| Integrin α5 | | | Xenopus laevis; alternative polyadenylation occurs in the embryo |
| Interleukin-8 receptor α | | | Human; two mRNAs equally abundant in neutrophils |
| Iron regulatory protein 2 (IRP2) | | Intracellular iron levels | Human, rat; RNA binding protein whose affinity for its binding site is modulated by intracellular iron levels; increase in proximal poly(A) site use with reciprocal decrease in distal poly(A) site use in iron-depleted cells |
| Ketohexokinase (fructokinase) | | | Human; two poly(A) sites; second is GAUAAA |
| Lamin B3 | | Testes | Mouse; germ cell (testes) specific RNA processing of lamin B2 generates lamin B3 |
| Lipoprotein lipase | 2 | Many cell types | Human; longer transcript predominates in skeletal and cardiac muscle; adipose tissue produces both forms of mRNA; longer transcript translated more efficiently than short one |
| Long chain acyl-CoA dehydrogenase (ACAD 1) | | Many cell types | Mouse; two poly(A) sites |
| Manganese superoxide dismutase | | Many cell types | Rat; five poly(A) sites; first two sites used in all tissues tested; proximal poly(A) site predominates in testes and liver, distal site used in heart, lung and kidney |
| Microtubule-associated protein 4 (MAP4) | | Many cell types | Mouse; 3'-UTR well conserved between mouse and human; first two sites used in all tissues tested; third site used in muscle; fourth sites used in testes, but first site predominates |
| Mitochondrial HMG-CoA synthase | 3 | | Rat; two poly(A) sites; AUUAAA and AUUAUC |
| N-Formyl peptide receptor (FMLF-R) | | Dibutryl cAMP treatment | Human; two-exon gene, at least two poly(A) sites; predominant use of proximal poly(A) site after treatment of HL60 human lymphoma cells with the differentiation agent dibutryl cAMP |
| NAD(P)H:quinone oxidoreductase | 3 | Mitomycin C treatment | Human colon cancer HCT 116 cells; two mRNAs; change in ratio after mitomycin C treatment |
| Non-muscle myosin heavy chain | | | Human; two poly(A) sites |
| mal-1 | | | Mouse; novel keratinocyte lipid-binding protein; tumor specific overexpression; two poly(A) sites, use of first one predominates |
| P-selectin glycoprotein ligand | | | Human, chromosome 12q24; major mRNA species 2.5 kb, minor species 4 kb |
| Paramyosin | | Developmental changes | Drosophila; use of two poly(A) sites is developmentally regulated |
| Phosphofructokinase (PFK) | | Developmental changes | Drosophila; use of three poly(A) sites is developmentally regulated |
| Platelet-derived growth factor (PDGF) | | | Three poly(A) signals |
| PR264/SC35 | 1 | Many cell types | Human splicing factor; ratio of different forms varies among six different cell lines tested |

TABLE 1-continued

Genes with alternative tandem poly(A) sites in the 3'-UTR

| Gene | Regulatory element[a] | Notable features Where seen | Comments |
|---|---|---|---|
| rab2 | 2 | Many cell types | Human Ras-related GTP binding protein; three potential poly(A) signals |
| RanGAP1 | | Testes | Human; activator of Ras-related nuclear GTPase Ran, shows testes-specific polyadenylation |
| Renal glutaminase | | Many cell types | Rat; ratio of poly(A) site use varies in different cell lines |
| RHOA protooncogene | 2 | | Human Ras-related GTP binding protein; found in breast cancer cell lines; three poly(A) sites |
| Senescence marker protein-30 (SMP-30) | | | Rat; two poly(A) sites |
| ser, putative oncogene associated with myeloid leukemogenesis | | Many cell types | Human, mouse; ratio of two mRNAs varies in different cell types and five cell lines tested; shorter mRNA predominates in liver and kidney |
| Soluble angiotensin binding protein | 3 | | Porcine; two poly(A) sites, first in GAUAAA; longer transcript may be regulated by SINE element in 3'-UTR |
| Splicing factor 9G8 | | Many cell types | Human; two poly(A) sites; pre-mRNA also subjected to alternative splicing |
| Steel | 3 | | Murine; encodes stem cell factor (SCF); distal poly(A) site used predominantly; 3'-UTR is 4.4 kb |
| Suppressor of forked su(f) | | | Drosophila; three mRNAs |
| Syndecan-1 | | | Mouse; two poly(A) sites |
| Tissue inhibitor of metalloproteinases-2 (TIMP-2) | 2 | | Human; two stable transcripts |
| Tissue inhibitor of metalloproteinases-3 (TIMP-3) | | TPA treatment | Murine; three transcripts of 2.3, 2.8 and 4.6 kb. 4.6 kb most abundant. All three transcripts induced in pre-neoplastic JB6 cells treated with TPA |
| Transforming growth factor alpha (TGF α) | 3 | | Human; five possible poly(A) sites but only two mRNAs detected; use of distal poly(A) site (AAUGAA) predominates in most tissues |
| Triose phosphate isomerase | 3 | Testes | Rat; 1.4 kb mRNA found in most tissues and in somatic cells of testes; its level increases after retinol treatment; the 1.5 kb species is detected only in haploid spermatids |
| Tryptophanyl-tRNA synthetase | | | Murine, human; two poly(A) sites; first is AAUCAA |
| Tubulin polycistronic pre-mRNA | | | Trypanosomes; transcription unit undergoes trans-splicing and alternative polyadenylation, which may be coupled in this system |
| Vascular endothelial growth factor (VEGF) | 1 | Hypoxia | Rat; two poly(A) sites; regulation of poly(A) site use by hypoxia |
| WNT-5A | | | Human; expression in early embryogenesis |
| ZAKI-4 | 2 | Many cell types | Human thyroid hormone-responsive gene; two mRNAs, first poly(A) signal is AUUAAA; short mRNA predominates in heart and brain, trace amounts found in liver; long mRNA predominates in skeletal muscle; no messages detected in placenta, lung, kidney, pancreas |

[a]Regulatory element key: 1, one mRNA more stable than another; 2, mRNA stability differences suggested from sequence but subsequently RNAs found to be equally stable; 3, mRNA differences in stability or translation suggested from sequence but not tested; 4, one mRNA found to be better translated than another, in vivo or in vitro.

TABLE 2

Genes with multiple poly(A) sites in competition with splice sites; 'in/terminal' exons

| Gene | Notes on regulation |
|---|---|
| (2'–5') Oligo A synthetase | Transcription induced by interferon-β; distal poly(A) site favored after inductin; proximal poly(A) site used predominantly during basal transcription |
| β-Spectrin | Proximal poly(A) site used exclusively in erythroid cells; default pattern of pre-mRNA processing uses distal poly(A) site |
| C3b/C4b receptor (complement receptor type 1) | Use of proximal poly(A) site yields secreted form of receptor; predominant membrane-bound receptor is generated by use of distal poly(A) site |
| Cek5 | Chicken receptor protein-tyrosine kinase of the Eph subfamily; use of the proximal poly(A) site yields secreted form of kinase, whose expression is low relative to the full-length Cek5 receptor |
| Epidermal growth factor (EGF) receptor; human, chicken | Proximal poly(A) site leads to production of secreted form of receptor, which can inhibit the activities of the membrane-bound receptor |
| *exuperantia* (*exu*) | Drosophila gene required for both oogenesis and spermatogenesis that undergoes sex-specific alternative pre-mRNA processing; tra-2 gene required for male-specific RNA processing |
| Fibrinogen γ-chain | Rat pre-mRNA undergoes liver-specific choice of proximal poly(A) site; other cell types always use distal poly(A) site |
| Fibroblast growth factor (FGF) receptor | Secreted form of receptor generated by use of the proximal poly(A) site; membrane-bound forms are produced by use of distal poly(A) site; secreted form also binds FGF |
| GARS/AIRS/GART | Glycinamide ribonucleotide synthetase (GARS)/aminoamidazole ribonucleotide synthetase |

TABLE 2-continued

Genes with multiple poly(A) sites in competition with splice sites; 'in/terminal' exons

| Gene | Notes on regulation |
| --- | --- |
| | (AIRS)/glycinamide ribonucleotide formyltransferase (GART); enzyme required for purine synthesis; use of proximal site corresponds to production of the monofunctional enzyme; use of the distal site yields the trifunctional enzyme; all tissues examined favor distal poly(A) site |
| Glucocorticoid receptor | β form of receptor produced by use of the proximal poly(A) site; more abundant α form uses the distal poly(A) site |
| HER2/neu receptor | Protein tyrosine kinase receptor in which membrane-bound form is produced from mRNA using the distal poly(A) site; use of proximal poly(A) site leads to shorter, intracellular form of the receptor; use of the proximal and distal poly(A) sites varies greatly in different tumor cell lines |
| Hepatocyte nuclear factor (HNF1/vHNF1) | Hepatocyte nuclear factor homeoprotein family important for liver-specific expression of a number of genes; poly(A) site choice and intron inclusion contribute to the generation of HNF1 isoforms, all of which contain different C-terminal domains, have distinct effects on transcription and can form homo- and heterodimers; mRNA levels for these isoforms vary in different tissue types and in some fetal versus adult tissues |
| Ig α heavy chain | Use of proximal poly(A) site produces mRNA encoding secreted form of antibody; use of the distal poly(A) site generates mRNA for membrane-bound antigen receptor; secretory-specific mRNA dominant in plasma cells whereas there are equal amounts of the two mRNAs in mature or memory B cells |
| Ig ε heavy chain | Pattern of regulation similar to Ig α heavy chain pre-mRNAs |
| Ig γ heavy chain | Pattern of regulation similar to Ig α heavy chain pre-mRNAs |
| Ig μ heavy chain | Pattern of regulation similar to Ig α and to other Ig heavy chain pre-mRNAs; can also include transcription terminaton as a mechanism of proximal poly(A) site selection |
| Leukemia inhibitory factor receptor α-chain | Member of hemopoietin receptor family; murine gene produces a secreted [proximal poly(A) site] and membrane-bound form [distal poly(A) site], with increase in the secreted form during pregnancy |
| Nuclear factor I-B3 | Distal poly(A) site favored in all tissues examined, proximal poly(A) sites used in heart and skeletal muscle; protein encoded by the shorter mRNA acts as a transcriptional repressor |
| Plasma membrane $Ca^{2+}$-ATPase isoform 3 | Use of proximal poly(A) site specific to skeletal muscle and brain |
| Poly(A) polymerase | Component of polyadenylation complex; six iosoforms generated via alternative splicing and polyadenylation; some isoforms found in all tissues examined, others show tissue-specific expression; use of one of three proximal poly(A) sites yields forms that contain the polymerase domain but not the serine/threonine-rich domain and nuclear localization signal (see also Table 3) |
| Sarco/endoplasmic reticulum $Ca^{2+}$-ATPase (SERCA) | Five protein isoforms are generated from three different SERCA genes plus alternative processing events; regulation of expression is both developmental and tissue specific and is suggested to be at the level of splicing rather thatn polyadenylation; two SERCA2 protein isoforms are translated from four different mRNAs generated by tissue-dependent alternative processing, one of which is brain specific; SERCA2a protein is muscle specific, SERCA2b is found in non-muscle tissues and smooth muscle |
| Secretory $PLA_2$ receptor | Receptor has similar structural organization to macrophage mannose receptor; acts as a mediator of inflammatory processes; secreted form of phospholipase$A_2$ receptor found in human kidney; membrane bound receptor is widely expressed, including in kidney |
| Thyroid hormone receptor α (c-erbA-1) | Proximal poly(A) site yields α1, which binds thyroid hormone; distal poly(A) site produces α2, which cannot bind thyroid hormone; ratio of two mRNAs varies in different tissues; α2 transcript overlaps with gene transcribed in opposite direction, Rev-ErbAα |

TABLE 3

Genes with multiple alternative 3'-terminal exons; skipped exons

| Gene | Notes on regulation |
| --- | --- |
| α-Tropomyosin | At least four poly(A) sites; proximal poly(A) site used in striated muscle and distal poly(A) site used in smooth muscle and fibroblasts; three of the poly(A) sites used in brain |
| Adenovirus major late transcription unit | Five poly(A) sites; the proximal poly(A) site, L1, used predominantly in early infection: L3 dominates late in infection |
| β-Tropomyosin | Proximal poly(A) site used exclusively in skeletal muscle; other cell types use the distal poly(A) site; regulation may be at the level of splice site choice |
| Calcitonin/calcitonin gene-related peptide (CGRP) | Proximal poly(A) site used in most cell types, generating the mRNA for calcitonin; distal poly(A) site used exclusively in neuronal cells, leading to production of CGRP |
| doublesex (dsx) | Drosophila gene required for somatic sexual differentiation that undergoes sex-specific alternative pre-mRNA processing; tra-2 protein required for regulated RNA processing and acts through its binding site in the dsx pre-mRNA |
| Epidermal growth factor (EGF) receptor; rat | Proximal poly(A) site leads to production of secreted form of receptor, which can inhibit the activities of the membrane-bound receptor; differs from human and chicken isoforms (see Table 2) |
| FLT4 receptor tyrosine kinase | Ratio of the mRNAs using the proximal or distal poly(A) site varies in different cell lines |
| Neural cell adhesion molecule (NCAM) | Ratio of the mRNAs produced varies in different cell types |
| Plasma α(1,3)-fucosyltransferase (FUT6) | Two poly(A) sites are used equally in liver; proximal poly(A) site favored in colon; distal poly(A) site used predominantly in kidney |
| Poly(A) polymerase | Component of polyadenylation complex; six isoforms generated via alternative splicing and polyadenylation; some isoforms found in all tissues examined, others show tissue-specific |

TABLE 3-continued

Genes with multiple alternative 3'-terminal exons; skipped exons

| Gene | Notes on regulation |
| --- | --- |
| | expression; use of one of three proximal poly(A) sites yields forms that contain the polymerase domain but not the serine/threonine-rich domain and nuclear localization signal (three exons also composite; see Table 2) |
| Unique human gene of unknown function | Spans over 230 kb in human chromosome 8p11-12; codes multiple proteins sharing RNA binding motifs |

The present invention is directed to identifying a target nucleic acid sequence which is predictive of a preselected disease state or biological condition. The disease states or biological conditions include, but are not limited to, nucleic acids known to be important during inflammation, cardiovascular disease, pain, cancer, arthritis, trauma, obesity, Huntingtons, neurological disorders, hyperproliferative conditions, neoplastic states or conditions, Lupus erythematosis, and many other diseases or disorders.

From analysis of Expressed Sequenced Tags (ESTs), it has been found that mRNA transcripts are much more heterogeneous than previously anticipated. Alternative transcript forms of mRNA molecules can be identified by using ESTs from a variety of databases. For example, preferred databases include, for example, Online Mendelian Inheritance in Man (OMIM), the Cancer Genome Anatomy Project (CGAP), GenBank, EMBL, PIR, SWISS-PROT, and the like. OMIM, which is a database of genetic mutations associated with disease, was developed, in part, for the National Center for Biotechnology Information (NCBI). OMIM can be accessed through the world wide web of the Internet, at, for example, ncbi.nlm.nih.gov/Omim/. CGAP, which is an interdisciplinary program to establish the information and technological tools required to decipher the molecular anatomy of a cancer cell. CGAP can be accessed through the world wide web of the Internet, at, for example, ncbi.nlm.nih.gov/ncicgap/. Some of these databases may contain complete or partial nucleotide sequences. In addition, alternative transcript forms can also be selected from private genetic databases. Alternatively, alternative transcript forms can be selected from available publications or can be determined especially for use in connection with the present invention.

After an alternative transcript form is selected or provided, the nucleotide sequence of the alternative transcript form preferably is determined. In one embodiment of the invention, the nucleotide sequence of the nucleic acid target is determined by scanning at least one genetic database or is identified in available publications. Preferred databases known and available to those skilled in the art include, for example, the Expressed Gene Anatomy Database (EGAD) and Unigene-Homo Sapiens database (Unigene), GenBank, and the like. EGAD contains a non-redundant set of human transcript (HT) sequences and can be accessed through the world wide web of the Internet, at, for example, tigr.org/tdb/egad/egad.html. Unigene is a system for automatically partitioning GenBank sequences into a non-redundant set of gene-oriented clusters. Each Unigene cluster contains sequences that represent a unique gene, as well as related information such as the tissue types in which the gene has been expressed and map location.

In addition, Unigene contains hundreds of thousands of novel expressed sequence tag (EST) sequences. Unigene can be accessed through the world wide web of the Internet, at, for example, ncbi.nlm.nih.gov/UniGene/. These databases can be used in connection with searching programs such as, for example, Entrez, which is known and available to those skilled in the art, and the like. Entrez can be accessed through the world wide web of the Internet, at, for example, ncbi.nlm.nih.gov/Entrez/. Preferably, the most complete nucleic acid sequence representation available from various databases is used. The GenBank database, which is known and available to those skilled in the art, can also be used to obtain the most complete nucleotide sequence. GenBank is the NIH genetic sequence database and is an annotated collection of all publicly available DNA sequences. GenBank is described in, for example, *Nuc. Acids Res.*, 1998, 26, 1–7, which is incorporated herein by reference in its entirety, and can be accessed by those skilled in the art through the world wide web of the Internet, at, for example, ncbo.nlm.nih.gov/Web/GenBank/indes.html. Alternatively, partial nucleotide sequences of nucleic acid targets can be used when a complete nucleotide sequence is not available.

Alternative transcript forms can be generated from individual ESTs which are within each of the databases by computer software which generates contiguous sequences. In another embodiment of the present invention, the nucleotide sequence of the nucleic acid target is determined by assembling a plurality of overlapping ESTs. The EST database (dbEST), which is known and available to those skilled in the art, comprises approximately one million different human mRNA sequences comprising from about 500 to 1000 nucleotides, and various numbers of ESTs from a number of different organisms. dbEST can be accessed through the world wide web of the Internet, at, for example, ncbi.nlm.nih.gov/dbEST/index.html. These sequences are derived from a cloning strategy that uses cDNA expression clones for genome sequencing. ESTs have applications in the discovery of new genes, mapping of genomes, and identification of coding regions in genomic sequences. Another important feature of EST sequence information that is becoming rapidly available is tissue-specific gene expression data. This can be extremely useful in targeting selective gene(s) for therapeutic intervention. Since EST sequences are relatively short, they must be assembled in order to provide a complete sequence. Because every available clone is sequenced, it results in a number of overlapping regions being reported in the database. The end result is the elicitation of alternative transcript forms from, for example, normal cells and cancer cells.

Assembly of overlapping ESTs extended along both the 5' and 3' directions results in a full-length "virtual transcript." The resultant virtual transcript may represent an already characterized nucleic acid or may be a novel nucleic acid with no known biological function. The Institute for Genomic Research (TIGR) Human Genome Index (HGI) database, which is known and available to those skilled in the art, contains a list of human transcripts. TIGR can be accessed through the world wide web of the Internet, at, for example, tigr.org. The transcripts were generated in this manner using TIGR-Assembler, an engine to build virtual transcripts and which is known and available to those skilled in the art. TIGR-Assembler is a tool for assembling large sets of overlapping sequence data such as ESTs, BACs, or small genomes, and can be used to assemble eukaryotic or prokaryotic sequences. TIGR-Assembler is described in, for example, Sutton, et al., *Genome Science & Tech.*, 1995, 1, 9–19, which is incorporated herein by reference in its entirety, and can be accessed through the file transfer program of the Internet, at, for example, tigr.org/pub/software/ TIGR. assembler. In addition, GLAXO-MRC, which is known and available to those skilled in the art, is another protocol for constructing virtual transcripts. In addition, "Find Neighbors and Assemble EST Blast" protocol, which runs on a UNIX platform, has been developed by Applicants to construct virtual transcripts. PHRAP is used for sequence assembly within Find Neighbors and Assemble EST Blast. PHRAP can be accessed through the world wide web of the Internet, at, for example, chimera.biotech.washington.edu/ uwgc/tools/phrap.htm. Identification of ESTs and generation of contiguous ESTs to form full length RNA molecules is described in detail in U.S. application Ser. No. 09/076,440, which is incorporated herein by reference in its entirety.

The members of a set of mRNA molecules are compared. Preferably, the set of mRNA molecules is a set of alternative transcript forms of mRNA. Preferably, the members of the set of alternative transcript forms of RNA include at least one member which is associated, or whose encoded protein is associated, with a disease state or biological condition. For example, a set of mRNA molecules for the mdm2 oncogene are compared. At least one of the members of the set of mRNA alternative transcript forms is associated with cancer, as described above. Thus, comparison of the members of the set of mRNA molecules results in the identification of at least one alternative transcript form of RNA which is associated, or whose encoded protein is associated, with a disease state or biological condition. In a preferred embodiment of the invention, the members of the set of mRNA molecules are from a common gene. In another embodiment of the invention, the members of the set of mRNA molecules are from a plurality of genes. In another embodiment of the invention, the members of the set of mRNA molecules are from different taxonomic species. Nucleotide sequences of a plurality of nucleic acids from different taxonomic species can be identified by performing a sequence similarity search, an ortholog search, or both, such searches being known to persons of ordinary skill in the art.

Sequence similarity searches can be performed manually or by using several available computer programs known to those skilled in the art. Preferably, Blast and Smith-Waterman algorithms, which are available and known to those skilled in the art, and the like can be used. Blast is NCBI's sequence similarity search tool designed to support analysis of nucleotide and protein sequence databases. Blast can be accessed through the world wide web of the Internet, at, for example, ncbi.nlm.nih.gov/BLAST/. The GCG Package provides a local version of Blast that can be used either with public domain databases or with any locally available searchable database. GCG Package v9.0 is a commercially available software package that contains over 100 interrelated software programs that enables analysis of sequences by editing, mapping, comparing and aligning them. Other programs included in the GCG Package include, for example, programs which facilitate RNA secondary structure predictions, nucleic acid fragment assembly, and evolutionary analysis. In addition, the most prominent genetic databases (GenBank, EMBL, PIR, and SWISS-PROT) are distributed along with the GCG Package and are fully accessible with the database searching and manipulation programs. GCG can be accessed through the Internet at, for example, http://www.gcg.com/. Fetch is a tool available in GCG that can get annotated GenBank records based on accession numbers and is similar to Entrez. Another sequence similarity search can be performed with GeneWorld and GeneThesaurus from Pangea. GeneWorld 2.5 is an automated, flexible, high-throughput application for analysis of polynucleotide and protein sequences. GeneWorld allows for automatic analysis and annotations of sequences. Like GCG, GeneWorld incorporates several tools for homology searching, gene finding, multiple sequence alignment, secondary structure prediction, and motif identification. GeneThesaurus 1.0 tm is a sequence and annotation data subscription service providing information from multiple sources, providing a relational data model for public and local data.

Another alternative sequence similarity search can be performed, for example, by BlastParse. BlastParse is a PERL script running on a UNIX platform that automates the strategy described above. BlastParse takes a list of target accession numbers of interest and parses all the GenBank fields into "tab-delimited" text that can then be saved in a "relational database" format for easier search and analysis, which provides flexibility. The end result is a series of completely parsed GenBank records that can be easily sorted, filtered, and queried against, as well as an annotations-relational database.

Preferably, the plurality of nucleic acids from different taxonomic species which have homology to the target nucleic acid, as described above in the sequence similarity search, are further delineated so as to find orthologs of the target nucleic acid therein. An ortholog is a term defined in gene classification to refer to two genes in widely divergent organisms that have sequence similarity, and perform similar functions within the context of the organism. In contrast, paralogs are genes within a species that occur due to gene duplication, but have evolved new functions, and are also referred to as isotypes. Optionally, paralog searches can also be performed. By performing an ortholog search, an exhaustive list of homologous sequences from as diverse organisms as possible is obtained. Subsequently, these sequences are analyzed to select the best representative sequence that fits the criteria for being an ortholog. An ortholog search can be performed by programs available to those skilled in the art including, for example, Compare. Preferably, an ortholog search is performed with access to complete and parsed GenBank annotations for each of the sequences. Currently, the records obtained from GenBank are "flat-files", and are not ideally suited for automated analysis. Preferably, the ortholog search is performed using a Q-Compare program. Preferred steps of the Q-Compare protocol are described in the flowchart set forth in U.S. Ser. No. 09/076,440, U.S. Pat. No. 6,221,587, incorporated herein by reference.

Preferably, interspecies sequence comparison is performed using Compare, which is available and known to those skilled in the art. Compare is a GCG tool that allows pair-wise comparisons of sequences using a window/ stringency criterion. Compare produces an output file containing points where matches of specified quality are found. These can be plotted with another GCG tool, DotPlot.

Once the members of the set of mRNA molecules are compared, at least one molecular interaction site from among those that are present in the members of the set is identified. The molecular interaction site is present in the alternative transcript form of the mRNA which is likely associated, or whose encoded protein is likely associated, with a disease state or biological condition. The molecular interaction site is identified by procedures well known to the skilled artisan. The molecular interaction site can be identified based on the nucleic acid sequence of the particular alternative transcript form of the mRNA or can be based on secondary structures presented within the alternative transcript form of the mRNA.

Molecular interaction sites are small, usually less than 30 nucleotides, independently folded, functional subdomains contained within a larger RNA molecule. Determining whether a particular alternative transcript form contains a molecular interaction site based on secondary structure can be performed by a number of procedures known to those skilled in the art. Determination of secondary structure is preferably performed by self complementarity comparison, alignment and covariance analysis, secondary structure prediction, or a combination thereof.

In one embodiment of the invention, secondary structure analysis is performed by alignment and covariance analysis. Numerous protocols for alignment and covariance analysis are known to those skilled in the art. Preferably, alignment is performed by ClustalW, which is available and known to those skilled in the art. ClustalW is a tool for multiple sequence alignment that, although not a part of GCG, can be added as an extension of the existing GCG tool set and used with local sequences. ClustalW can be accessed through the world wide web of the Internet, at, for example, dot.imgen.bcm.tmc.edu:9331/multi-align/Options/clustalw.html. ClustalW is also described in Thompson, et al., *Nuc. Acids Res.*, 1994, 22, 4673–4680, which is incorporated herein by reference in its entirety. These processes can be scripted to automatically use conserved UTR regions identified in earlier steps. Seqed, a UNIX command line interface available and known to those skilled in the art, allows extraction of selected local regions from a larger sequence. Multiple sequences from many different species can be clustered and aligned for further analysis.

Covariation is a process of using phylogenetic analysis of primary sequence information for consensus secondary structure prediction. Covariation is described in the following references, each of which is incorporated herein by reference in their entirety: Gutell, et a., "Comparative Sequence Analysis Of Experiments Performed During Evolution" In Ribosomal RNA Group I Introns, Green, Ed., Austin:Landes, 1996; Gautheret, et al., *Nuc. Acids Res.*, 1997, 25, 1559–1564; Gautheret, et al., *RNA*, 1995, 1, 807–814; Lodmell, et al., *Proc. Natl. Acad. Sci. USA*, 1995, 92, 10555–10559; Gautheret, et al.,*J. Mol. Biol.*, 1995, 248, 27–43; Gutell, *Nuc. Acids Res.*, 1994, 22, 3502–3517; Gutell, *Nuc. Acids Res.*, 1993, 21, 3055–3074; Gutell, *Nuc. Acids Res.*, 1993, 21, 3051–3054; Woese, *Proc. Natl. Acad. Sci. USA*, 1989, 86, 3119–3122; and Woese, et al., *Nuc. Acids Res.*, 1980, 8, 2275–2293. Preferably, covariance software is used for covariance analysis. Preferably, Covariation, a set of programs for the comparative analysis of RNA structure from sequence alignments, is used. Covariation uses phylogenetic analysis of primary sequence information for consensus secondary structure prediction. Covariation can be obtained through the world wide web of the Internet, at, for example, mbio.ncsu.edu/RnaseP/info/programs/programs.html. A complete description of a version of the program has been published (Brown, J. W. 1991 Phylogenetic analysis of RNA structure on the Macintosh computer. CABIOS7:391–393). The current version is v4.1, which can perform various types of covariation analysis from RNA sequence alignments, including standard covariation analysis, the identification of compensatory base-changes, and mutual information analysis. The program is well-documented and comes with extensive example files. Compiled as a stand-alone program; it does not require Hypercard (although a much smaller 'stack' version is included). This program will run in any Macintosh environment running MacOS v7.1 or higher. Faster processor machines (68040 or PowerPC) is suggested for mutual information analysis or the analysis of large sequence alignments.

In another embodiment of the invention, secondary structure analysis is performed by secondary structure prediction. There are a number of algorithms that predict RNA secondary structures based on thermodynamic parameters and energy calculations. Preferably, secondary structure prediction is performed using either M-fold or RNA Structure 2.52. M-fold can be accessed through the world wide web of the Internet, at, for example, ibc.wustl.edu/-zuker/ma/form2.cgi. or can be downloaded for local use on UNIX platforms. M-fold is also available as a part of GCG package. RNA Structure 2.52 is a windows adaptation of the M-fold algorithm and can be accessed through the world wide web of the Internet, at, for example, 128.151.176.70/RNAstructure.html.

In another embodiment of the invention, secondary structure analysis is performed by self complementarity comparison. Preferably, self complementarity comparison is performed using Compare, described above. More preferably, Compare can be modified to expand the pairing matrix to account for G-U or U-G base pairs in addition to the conventional Watson-Crick G-C/C-G or A-U/U-A pairs. Such a modified Compare program (modified Compare) begins by predicting all possible base-pairings within a given sequence. As described above, a small but conserved region, preferably a UTR, is identified based on primary sequence comparison of a series of orthologs. In modified Compare, each of these sequences is compared to its own reverse complement. Allowable base-pairings include Watson-Crick A-U, G-C pairing and non-canonical G-U pairing. An overlay of such self complementarity plots of all available orthologs, and selection for the most repetitive pattern in each, results in a minimal number of possible folded configurations. These overlays can then be used in conjunction with additional constraints, including those imposed by energy considerations described above, to deduce the most likely secondary structure.

A result of the secondary structure analysis described above, whether performed by alignment and covariance, self complementarity analysis, secondary structure predictions, such as using M-fold or otherwise, is the identification of secondary structure in other alternative transcript forms. Exemplary secondary structures that may be identified include, but are not limited to, bulges, loops, stems, hairpins, knots, triple interacts, cloverleafs, or helices, or a combination thereof. Alternatively, new secondary structures may be identified.

In another embodiment of the invention, once the secondary structure of the conserved region has been identified, as described above, at least one structural motif molecular interaction site is identified. These structural motifs correspond to the identified secondary structures described above. For example, analysis of secondary structure by self complementation may provide one type of secondary structure, whereas analysis by M-fold may provide another secondary structure. All the possible secondary structures identified by secondary structure analysis described above are, thus, represented by a family of structural motifs.

Once the secondary structure(s) of the target nucleic acids, as well as the secondary structures of nucleic acids from different taxonomic species, have been identified, further alternative transcript forms of mRNAs can be identified by searching on the basis of structure, rather than by primary nucleotide sequence, as described above. Additional alternative transcript forms which have secondary structure similar or identical to the secondary structure found as described above can be identified by constructing a family of descriptor elements for the structural motifs described above, and identifying other nucleic acids having secondary structures corresponding to the descriptor elements. The combination of any or all of the nucleic acids having secondary structure can be compiled into a database. The entire process can be repeated with a different target nucleic acid to generate a plurality of different secondary structure groups which can be compiled into the database. Thus, databases of molecular interaction sites can be compiled by performing by the invention described herein.

After the hypothetical structure motifs are determined from the secondary structure analysis described above, a family of structure descriptor elements is constructed, as described in U.S. Ser. No. 09/076,440, U.S. Pat. No. 6,221,587, which is incorporated herein by reference in its entirety. Preferably, the structural motifs described above are converted into a family of descriptor elements. One skilled in the art is familiar with construction of descriptors. Structure descriptors are described in, for example, Laferriere, et al., *Comput. Appl. Biosci.*, 1994, 10, 211–212, incorporated herein by reference in its entirety. A different structure descriptor element is constructed for each of the structural motifs identified from the secondary structure analysis. Briefly, the secondary structure is converted to a generic text string. For novel motifs, further biochemical analysis such as chemical mapping or mutagenesis may be needed to confirm structure predictions. Descriptor elements may be defined to have various stringency. In addition, the descriptor elements can be defined to allow for a wobble. Thus, descriptor elements can be defined to have any level of stringency desired by the user.

After a family of structure descriptor elements is constructed, nucleic acids having secondary structure which correspond to the structure descriptor elements are identified. Preferably, nucleic acids having secondary structure which correspond to the structure descriptor elements are identified by searching at least one database, performing clustering and analysis, identifying orthologs, or a combination thereof. Thus, the identified alternative transcript forms have secondary structure which falls within the scope of the secondary structure defined by the descriptor elements. Thus, the identified alternative transcript forms have secondary structure identical to nearly identical, depending on the stringency of the descriptor elements, to the alternative transcript forms previously identified.

In one embodiment of the invention, nucleic acids having secondary structure which correspond to the structure descriptor elements are identified by searching at least one database. Any genetic database can be searched. Preferably, the database is a UTR database, which is a compilation of the untranslated regions in messenger RNAs. A UTR database is accessible through the Internet at, for example, ftp://area.ba.cnr.it/pub/embnet/database/utr/. Preferably the database is searched using a computer program, such as, for example, Rnamot, a UNIX-based motif searching tool available from Daniel Gautheret. Each "new" sequence that has the same motif is then queried against public domain databases to identify additional sequences. Results are analyzed for recurrence of pattern in UTRs of these additional ortholog sequences, as described below, and a database of RNA secondary structures is built. One skilled in the art is familiar with Rnamot. Briefly, Rnamot takes a descriptor string and searches any Fasta format database for possible matches. Descriptors can be very specific, to match exact nucleotide(s), or can have built-in degeneracy. Lengths of the stem and loop can also be specified. Single stranded loop regions can have a variable length. G-U pairings are allowed and can be specified as a wobble parameter. Allowable mismatches can also be included in the descriptor definition. Functional significance is assigned to the motifs if their biological role is known based on previous analysis.

In another embodiment of the invention, the nucleic acids identified by searching databases such as, for example, searching a UTR database using Rnamot, are clustered and analyzed so as to determine their location within the genome. The results provided by Rnamot simply identify sequences containing the secondary structure but do not give any indication as to the location of the sequence in the genome. Clustering and analysis is preferably performed with ClustalW, as described above.

In another embodiment of the invention, after clustering and analysis is performed as described above, orthologs are identified as described above. However, in contrast to the orthologs identified above, which were solely identified on the basis of their primary nucleotide sequences, these new orthologous sequences are identified on the basis of structure using the nucleic acids identified using Rnamot. Identification of orthologs is preferably performed by BlastParse or Q-Compare, as described above. In embodiments of the invention in which a database containing prokaryotic molecular interaction sites is compiled, it is preferable to refrain from finding human orthologs or, alternatively, discarding human orthologs when found.

Once the molecular interaction site of an alternative transcript form which is associated to a disease state or biological condition is identified, the nucleic acid sequence from said molecular interaction site is ascertained by routine methodology. The nucleic acid sequences, in turn, can be used to design targeting biomolecules, such as, for example, oligonucleotides, peptide nucleic acid molecules, ribozymes, and small molecules, which interact with the molecular interaction site. The methods of the invention further include contacting the nucleic acid sequence with biomolecules, such as, for example, an oligonucleotide or small molecule. The biomolecules preferably comprise toxin molecules. While there are a number of ways to prepare biomolecules comprising toxins, preferred methodologies are described in a U.S. patent application filed on even date herewith and assigned to the assignee of this invention. This application bear U.S. Ser. No. 09/200,107 filed on even date herewith assigned attorney docket number IBIS-0010, which is incorporated by reference herein in its entirety.

The following examples are meant to be exemplary of embodiments of the invention and are not meant to be limiting.

EXAMPLES

Example 1

Molecular Target in RNA Formed from Alternative Initiation and Splicing of the mdm2 Oncogene The mdm2 oncogene has been associated with a variety of human cancers. The protein encoded by mdm2 physically binds to the anti-oncogene p53 protein and interferes with its function as a tumor suppressor. The net result of suppression of a tumor suppressor is tumorigenesis. It was recently discovered that many tumor cells have greatly increased levels or mdm2 protein without a proportionate increase in mdm2 mRNA levels, suggesting that regulation of protein levels occurs downstream of transcription. It was discovered that cancer cells contain a form of the mdm2 mRNA that is different in the 5'-untranslated region. Both the normal and cancer-specific forms of the transcript encode an identical protein, since the heterogeneity is found upstream of the initiation of translation on the message.

The cancer-specific mdm2 RNA was found to contain three classes of unique structures shown in the box on the lower left side of the illustration. The first structure, shown labeled "unique exon structure" in FIG. 2, derives from unique sequences in Exon 1 that are not included in the mdm2 transcript found in normal cells. This structure contains two unique internal loops separated by a stack of 5 base pairs and adjacent to a cytosine rich stem loop. Analysis of all mRNA transcripts in the current release of genbank reveals that this structure is unique to the cancer-specific mdm2 transcript.

The second unique structure is found 3' to the first structure is shown in red and blue. It is comprised of mRNA originating from Exons 1 and 3, which are uniquely found adjacent to each other in the cancer-specific form. This structure, which is also unique, can only exist where these exons are spliced together because it contains parts of each.

The right hand structure in the box is derived exclusively from mRNA that is from Exon 3. This structure could potentially exist in both the cancer and normal forms of the message. However, in the normal form, this RNA is part of a different structure which is disfavored in the Exon 1/Exon3 junction form.

Example 2

The HER2/neu Receptor in Carcinoma Cells

The HER2 proto-oncogene encodes a protein that binds to the membrane of the cell and transduces signals through a tyrosine kinase activity. This protein has clearly demonstrated association with breast cancer. A product that targets this protein with a monoclonal antibody (Herceptin) has recently been approved for use by the FDA for the treatment of breast cancer.

It is known that the HER2 receptor mRNA exists in at least two forms (Mol. Cell. Biology 1993,2247–2257, which is incorporated herein by reference in its entirety). The two transcript forms are generated from alternative use of a splice site located 2050 nucleotides downstream from the start of the mRNA. In some cases the splice site is used to generate a transcript greater than 4,000 nucleotides. At other times, the splice site is not used. When it is not used, polyadenylation site downstream of the splice junction triggers termination and polyadenylation of the mRNA. An in-frame stop codon is then used to terminate the protein during translation. The truncated form of the protein contains the extracellular domain of the normal protein without the membrane anchor domain, which results in a secreted rather than a cell associated protein. Transfection studies have shown that the truncated form of HER2 produces a protein that is released from the cell results in resistance to the growth inhibiting effects of the monoclonal antibody used in cancer treatment. Thus, cells producing the truncated form of the mRNA are undesired because they may play a role in resistance to an otherwise useful drug.

Figure 3:
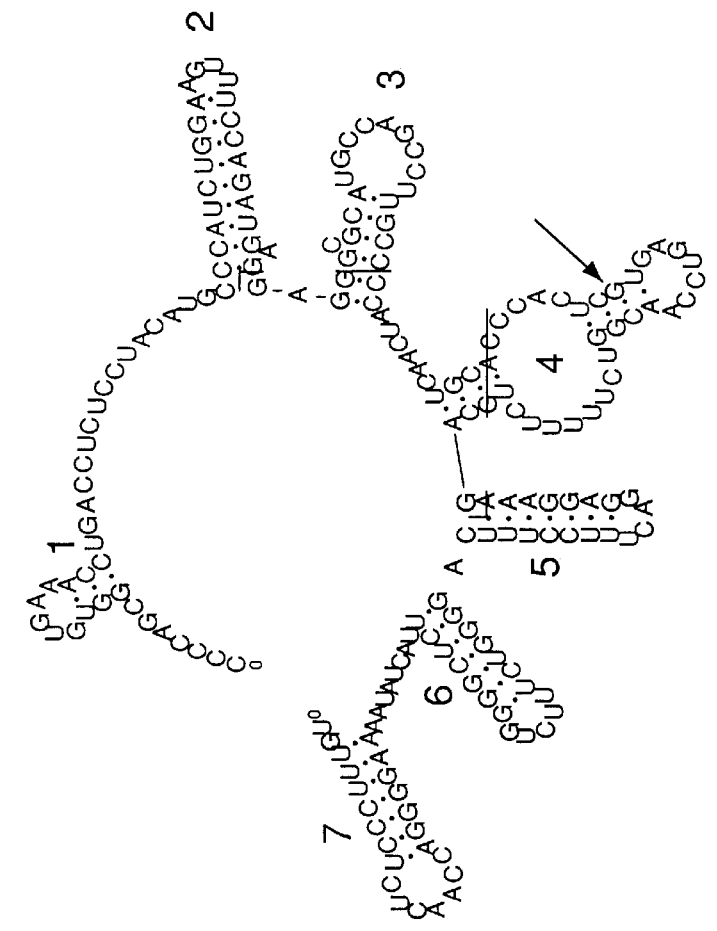
FIG. 3 illustrates Her 2 alternative transcript forms (SEQ ID NO: 3, left, and SEQ ID NO: 4, right).
Figure 3:
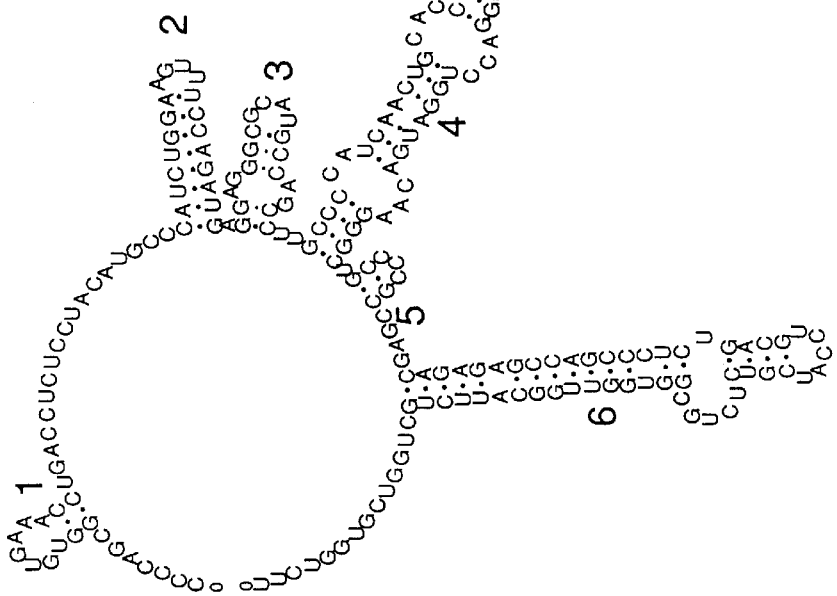

The truncated form of the transcript contains unique structures not found in the normal form (see, FIG. 3). The structure on the left is a portion of the normal form and the truncated form is on the right. The arrow indicated the location of the divergence between the two forms. Helical structures 1 and 2 are common to both transcript forms. Helicies 4 from both forms are comprised of RNA that is, in part, common to both forms and unique to each form. Thus, helix 4 in the truncated form is a unique target for proximity trigger technology, as is 5, 6 and 7 which are unique to the truncated form. Helix 3 is another example of a structure that is comprised of RNA sequence that is common to both forms of the RNA, but still different in shape as a result of the sequences around it. It is also a useful target for proximity trigger technology.

What is claimed is:

1. A method of identifying a target nucleic aid sequence, said nucleic acid sequence being predictive of a preselected disease state in cells containing the nucleic acid sequence comprising:

comparing members of a set of mRNA alternative transcript forms from a common gene, said alternative transcript forms being transcribed from identical DNA, said gene being predictive of said disease state in cells containing the gene;

identifying at least one molecular interaction site from among those present in said members of the set based on secondary structure of said mRNA alternative transcript forms; said molecular interaction site being present in cells likely to have said disease state; and ascertaining said target nucleic acid sequence from said molecular interaction site.

2. The method of claim 1 wherein said molecular interaction site is common among a plurality of said members.

3. The method of claim 1 wherein said gene codes for a protein not essential for maintaining the cells, disease state or condition.

4. The method of claim 1 further comprising contacting said nucleic acid sequence with an oligonucleotide or small molecule.

5. The method of claim 1 wherein said disease state is a hyperproliferative condition.

6. The method of claim 1 wherein said disease state is neoplastic.

7. The method of claim 1 wherein said disease state is a cancerous state.

8. The method of claim 1 wherein said disease state is Lupus erythematosis.

9. The method of claim 1 wherein said disease state is psoriasis.

* * * * *

SEQUENCE LISTING

```
<160> NUMBER OF SEQ ID NOS: 4

<210> SEQ ID NO 1
<211> LENGTH: 199
<212> TYPE: RNA
<213> ORGANISM: Homo sapiens

<400> SEQUENCE: 1
gaaacugggg agucuugagg gaccccgac uccaagcgcg aaaaccccgg auggugagga      60
gcagggaaau gugcaauacc aacaugucug uaccacuga uggugcugua accaccucac    120
agauuccagc uucggaacaa gagacccugg uuagaccaaa gccauugcuu uugaaguuau   180
uaaagucugu uggugcaca                                                 199

<210> SEQ ID NO 2
<211> LENGTH: 199
<212> TYPE: RNA
<213> ORGANISM: Homo sapiens
```

```
<400> SEQUENCE: 2
caguggcgau uggagggguag accuguggc acggacgcac gccacuuuuu cucugcugau      60
ccaggcaaau gugcaauacc aacaugucug uaccacuga uggugcugua accaccucac     120
agauuccagc uucggaacaa gagacccugg uuagaccaaa gccauugcuu uugaaguuau     180
uaaagucugu uggugcaca                                                 199

<210> SEQ ID NO 3
<211> LENGTH: 201
<212> TYPE: RNA
<213> ORGANISM: Homo sapiens

<400> SEQUENCE: 3
ccccagcggu gugaaaccug accucuccua caugcccauc uggaaguuuc cagaugagga      60
gggcgcaugc cagccuugcc ccaucaacug cacccacucc uguguggacc uggaugacaa     120
gggcugcccc gccgagcaga gagccagccc ucugacgucc aucgucucug cgguggluugg    180 cauucugcug gucgugucu u                                               201

<210> SEQ ID NO 4
<211> LENGTH: 195
<212> TYPE: RNA
<213> ORGANISM: Homo sapiens

<400> SEQUENCE: 4
ccccagcggu gugaaaccug accucuccua caugcccauc uggaaguuuc cagaugagga      60
gggcgcaugc cagccuugcc ccaucaacug cacccacucg ugaguccaac ggucuuuuuc     120
uccagaaagg aggacuuucc uuucaggggu cuuucugggg cucuuacuau aaaagggac     180 caacucuccc uuugu                                                    195
```